(12) United States Patent
Jiang et al.

(10) Patent No.: US 8,664,594 B1
(45) Date of Patent: Mar. 4, 2014

(54) ELECTRON-OPTICAL SYSTEM FOR HIGH-SPEED AND HIGH-SENSITIVITY INSPECTIONS

(75) Inventors: Xinrong Jiang, Palo Alto, CA (US); Liqun Han, Pleasanton, CA (US); Mohammed Tahmassebpur, San Ramon, CA (US); Salam Harb, Los Gatos, CA (US); John D. Greene, Santa Cruz, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 111 days.

(21) Appl. No.: 13/095,574

(22) Filed: Apr. 27, 2011

Related U.S. Application Data

(60) Provisional application No. 61/476,706, filed on Apr. 18, 2011.

(51) Int. Cl.
*G01N 23/00* (2006.01)
*G21K 7/00* (2006.01)

(52) U.S. Cl.
USPC ........... 250/306; 250/307; 250/310; 250/311; 250/492.1; 250/492.23; 313/361.1

(58) Field of Classification Search
USPC ......... 250/306, 307, 310, 311, 492.1, 492.23; 313/316.1
See application file for complete search history.

(56) References Cited

U.S. PATENT DOCUMENTS

| | | | |
|---|---|---|---|
| 3,930,181 A | 12/1975 | Pfeiffer | |
| 3,984,687 A | 10/1976 | Loeffler et al. | |
| 4,084,095 A | 4/1978 | Wolfe | |
| 4,952,814 A | 8/1990 | Huntzinger | |
| 5,886,357 A | 3/1999 | Kojima | |
| 6,011,269 A | 1/2000 | Veneklasen et al. | |
| 6,448,568 B1 | 9/2002 | Allen et al. | |
| 6,885,012 B2 * | 4/2005 | Tanaka et al. | 250/491.1 |
| 6,977,386 B2 | 12/2005 | Gerlach et al. | |
| 7,109,486 B1 | 9/2006 | Spallas et al. | |
| 7,427,765 B2 | 9/2008 | Buller et al. | |
| 7,615,746 B2 * | 11/2009 | Nagatomo et al. | 250/307 |
| 7,633,069 B2 | 12/2009 | Rafferty | |
| 7,800,075 B2 | 9/2010 | Buller et al. | |
| 7,821,187 B1 * | 10/2010 | Jiang et al. | 313/361.1 |
| 8,278,623 B2 * | 10/2012 | Tahmassebpur | 250/310 |
| 2002/0148971 A1 | 10/2002 | Sogard | |
| 2003/0155508 A1 * | 8/2003 | Suzuki et al. | 250/310 |
| 2005/0139789 A1 * | 6/2005 | Nagano et al. | 250/492.23 |
| 2007/0085033 A1 | 4/2007 | Buller et al. | |
| 2007/0257207 A1 * | 11/2007 | Frosien et al. | 250/492.3 |

(Continued)

*Primary Examiner* — Jack Berman
*Assistant Examiner* — Meenakshi Sahu
(74) *Attorney, Agent, or Firm* — Okamoto & Benedicto LLP

(57) ABSTRACT

The present disclosure provides an electron beam column with substantially improved resolution and/or throughput for inspecting manufactured substrates. The electron beam column comprises an electron gun, a scanner, an objective lens, and a detector. In accordance with one embodiment, the electron gun includes a gun lens having a flip-up pole piece configuration. In accordance with another embodiment, the scanner comprises a dual scanner having a pre-scanner and a main scanner, and the detector may be configured between the electron gun and the pre-scanner. In accordance with another embodiment, the electron beam column includes a continuously-variable aperture configured to select a beam current. Other embodiments relate to methods of using an electron beam column for automated inspection of manufactured substrates. In one embodiment, for example, an aperture size is adjusted to achieve a minimum spot size given a selected beam current and a column-condition domain being used.

9 Claims, 8 Drawing Sheets

(56) References Cited

U.S. PATENT DOCUMENTS

2008/0093561 A1 4/2008 Rafferty
2008/0308751 A1 12/2008 Buller et al.
2011/0114838 A1* 5/2011 Han et al. ..................... 250/307
2012/0181444 A1* 7/2012 Tahmassebpur .......... 250/396 R

* cited by examiner

ELECTRON-OPTICAL SYSTEM FOR HIGH-SPEED AND HIGH-SENSITIVITY INSPECTIONS

CROSS-REFERENCE TO RELATED APPLICATIONS

The present application claims the benefit of U.S. Provisional Patent Application No. 61/476,706, entitled "Electron-Optical System for High-Speed and High-Sensitivity Inspections," filed Apr. 18, 2011, the disclosure of which is hereby incorporated by reference.

BACKGROUND

1. Technical Field

The present invention relates generally to semiconductor manufacturing and related technologies. More particularly, the present invention relates to an electron beam column and methods for using the column in automated inspection and other applications.

2. Description of the Background Art

Automated electron beam inspection systems typically use an electron beam column to scan an electron beam across a region of a substrate surface to obtain image data. The present disclosure provides a novel and inventive electron beam column for use in automated electron beam inspection and other applications.

SUMMARY

The present disclosure provides an electron beam inspection (EBI) system with substantially improved resolution and/or throughput for inspecting manufactured substrates. The EBI system may include an electron beam column comprising an electron gun, a scanner, an objective lens, and a detector.

In accordance with one embodiment, the electron gun may include a gun lens having a flip-up pole piece configuration. In contrast, conventional electron guns have a flip-down pole piece configuration.

In accordance with another embodiment, the scanner may comprise a dual scanner having a pre-scanner and a main scanner, and the detector may be configured between the electron gun and the pre-scanner. In one particular embodiment, the electrodes of the dual scanner are tapered.

In accordance with another embodiment, the electron beam column may include a continuously-variable aperture configured to select a beam current. The continuously-variable aperture may be implemented as a square aperture formed by the edges of overlapping blades.

Other embodiments relate to methods of using an electron beam column for automated inspection of manufactured substrates. In one embodiment, for example, an aperture size may be adjusted to achieve a minimum spot size given a selected beam current and a column-condition domain being used. A column-condition domain may be defined, for example, by a landing energy and an electric field strength at the surface of the target substrate Other embodiments, aspects, and features are also disclosed herein.

DETAILED DESCRIPTION

Figure 1:
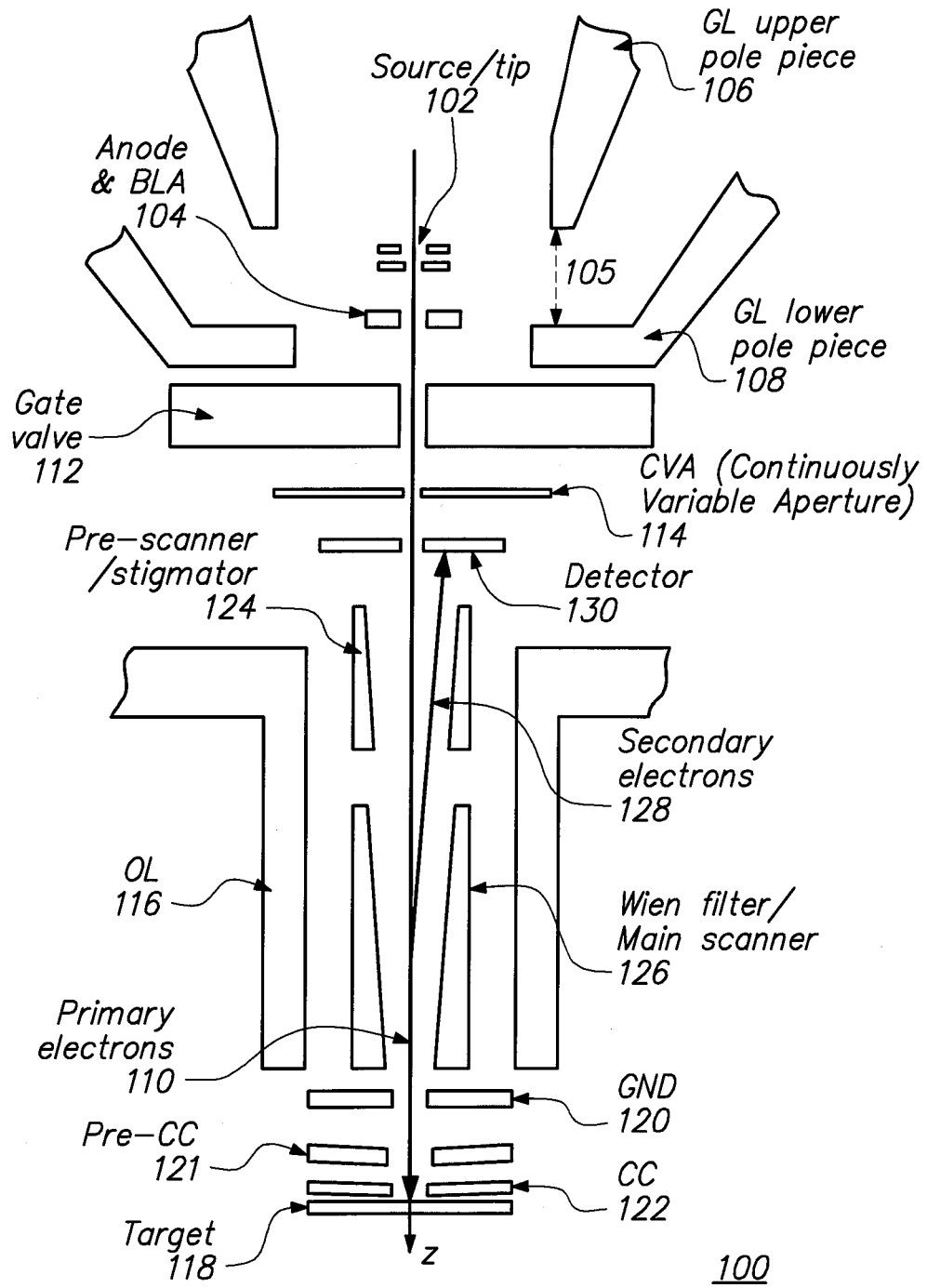
FIG. 1 is a schematic diagram of an electron-optical column for electron beam inspection in accordance with an embodiment of the invention.

FIG. 1 is a schematic diagram of an electron-optical column 100 for an electron beam inspection apparatus in accordance with an embodiment of the invention. The electron-optical column 100 includes innovative design features over previous electron-optical columns 100. The innovative design features result in the substantial improvement of the imaging resolution and/or throughput for the electron beam inspection apparatus. An innovative design for an electron-optical column is also described in commonly-owned U.S. patent application Ser. No. 12/958,174, filed Dec. 1, 2010, entitled "Electron Beam Column and Methods of Using Same."

The electron-optical column 100 includes a cathode source or emitter tip 102 which emits electrons and a gun lens (GL). The gun lens may include an upper pole piece 106 and a lower pole piece 108 in a magnetic field section and an anode and beam limiting aperture (BLA) 104 in an electric field section. The emitted electrons are accelerated through an opening in the anode and focused into a primary electron beam 110 which is directed along the optical axis of the column (defined as the z-axis) to an opening in a gate valve 112. The gate valve 112 divides the upper (gun) vacuum chamber from the lower (main) vacuum chamber.

After being extracted from the cathode source or emitter tip 102, the electrons are at a lower energy level defined as the "extraction energy" (EE). After acceleration by the gun lens, the electrons in the primary electron beam 110 are at a higher energy level defined as the "beam energy" (BE). In one example implementation, the EE level may be in a range of 4 to 7 keV, and the BE level may be in a range of 8 to 12 keV. The particular energy levels to be used depend on the particular implementation. In another example implementation, an ultra high BE of up to 35 keV may be used by providing a high voltage stand-off capability in a column which is very short in the z-dimension. The BE may be made variable to take advantage of high BE electron-optics for reducing electron-electron interactions without taking an extra high voltage risk.

Figure 2:
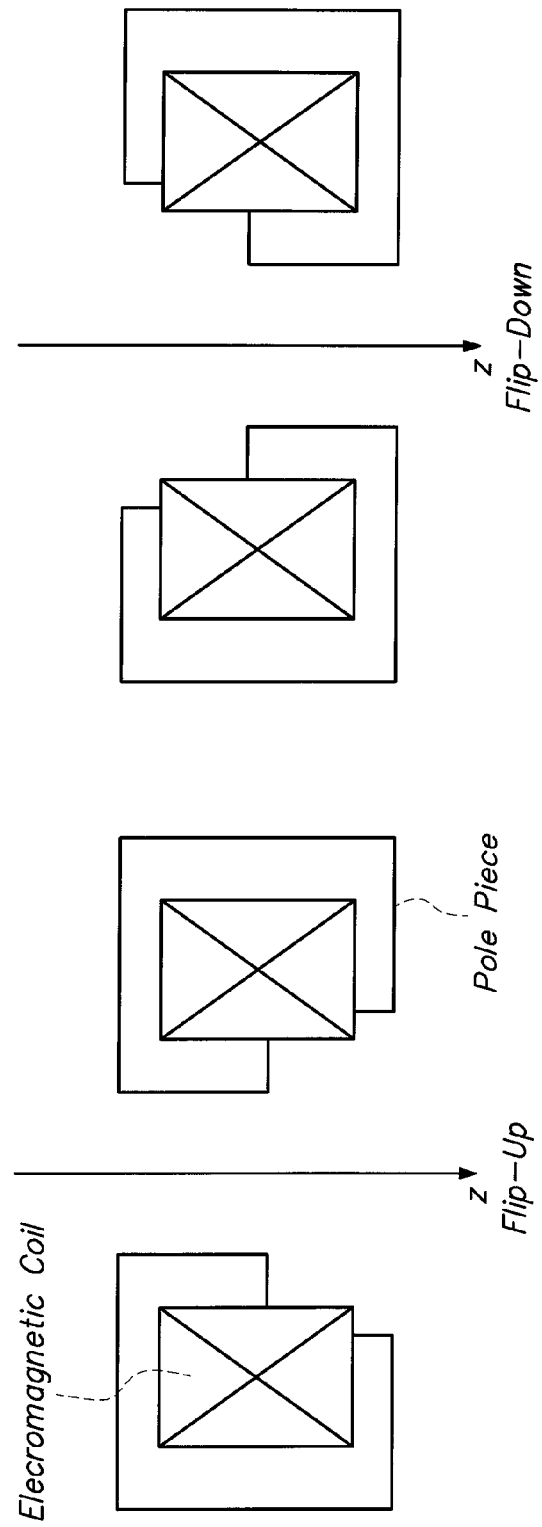
FIG. 2 depicts flip-up and flip-down pole piece configurations.

In accordance with an embodiment of the invention, the pole pieces of the magnetic field section of the gun lens in FIG. 1 are arranged in a flip-up pole piece configuration. In a flip-up pole piece configuration, the gap 105 between the upper and lower pole pieces (104 and 106) is positioned at the bottom of the pole pieces. In contrast, a conventional gun lens has pole pieces arranged in a flip-down pole piece configuration. In a flip-down pole piece configuration, the gap between the upper and lower pole pieces is positioned at the top of the pole pieces. FIG. 2 contrasts flip-up and flip-down pole piece configurations.

Figure 3A:
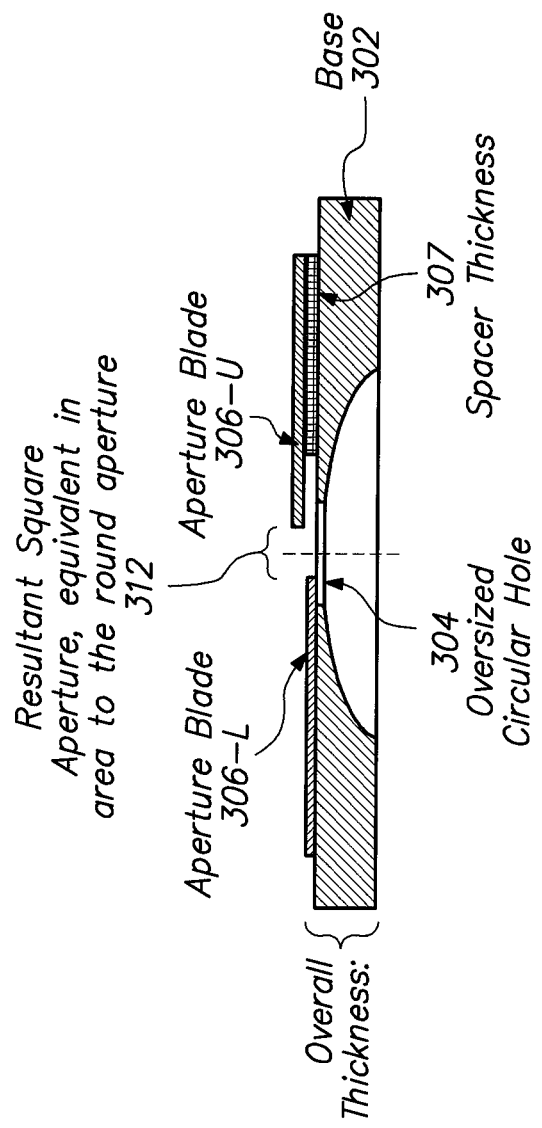
FIG. 3A shows a cross-sectional view of a square aperture with overlapping blades in accordance with an embodiment of the invention.
Figure 3B:
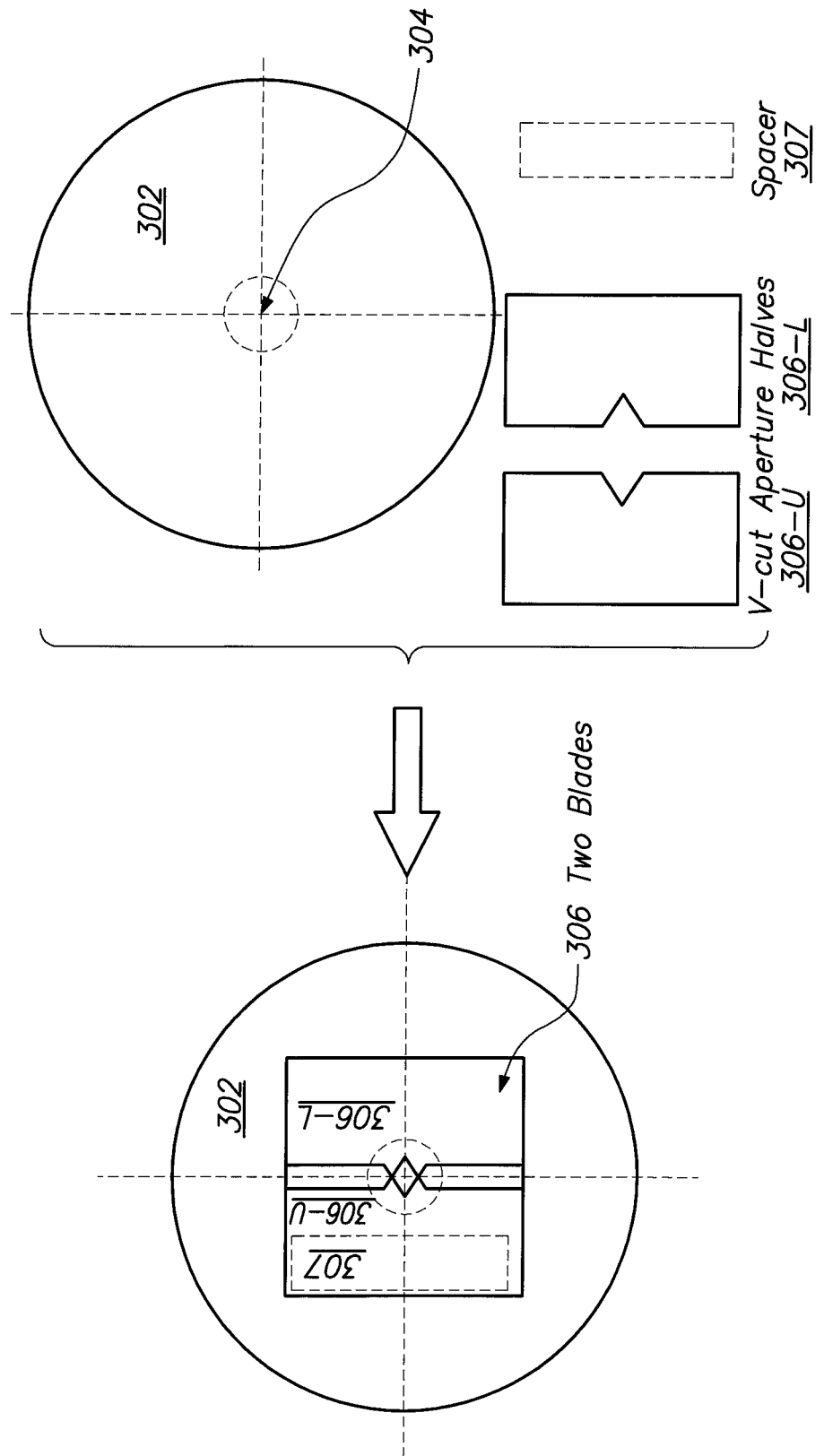
FIG. 3B shows a plan view of a square aperture which is formed by overlapping two V-cut blades in accordance with an embodiment of the invention.
Figure 3C:
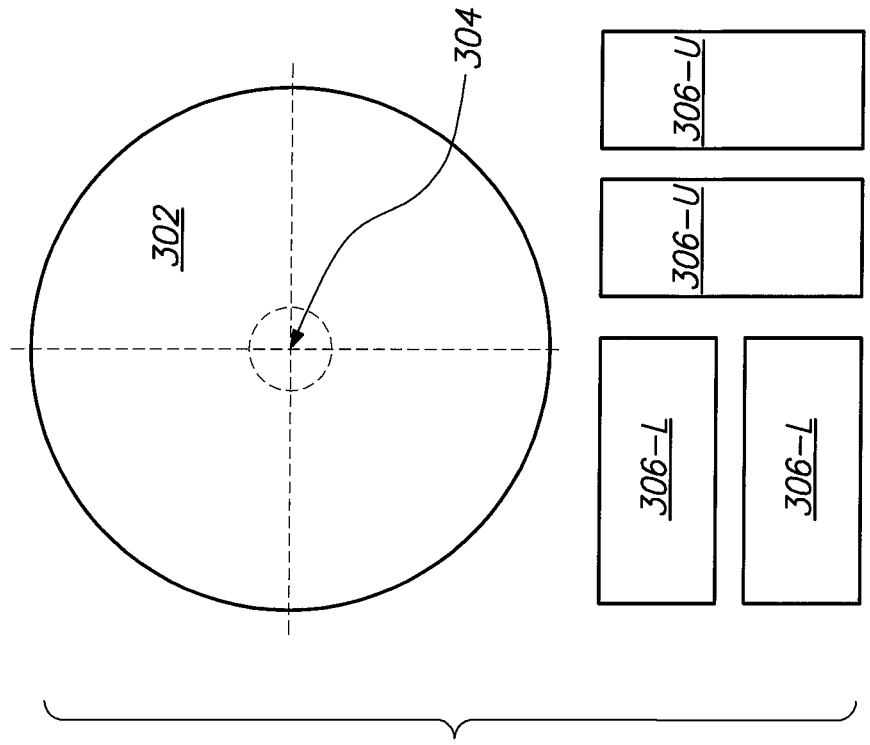
FIG. 3C shows a plan view of a square aperture which is formed by overlapping four rectangular blades in accordance with an embodiment of the invention.
Figure 3C:
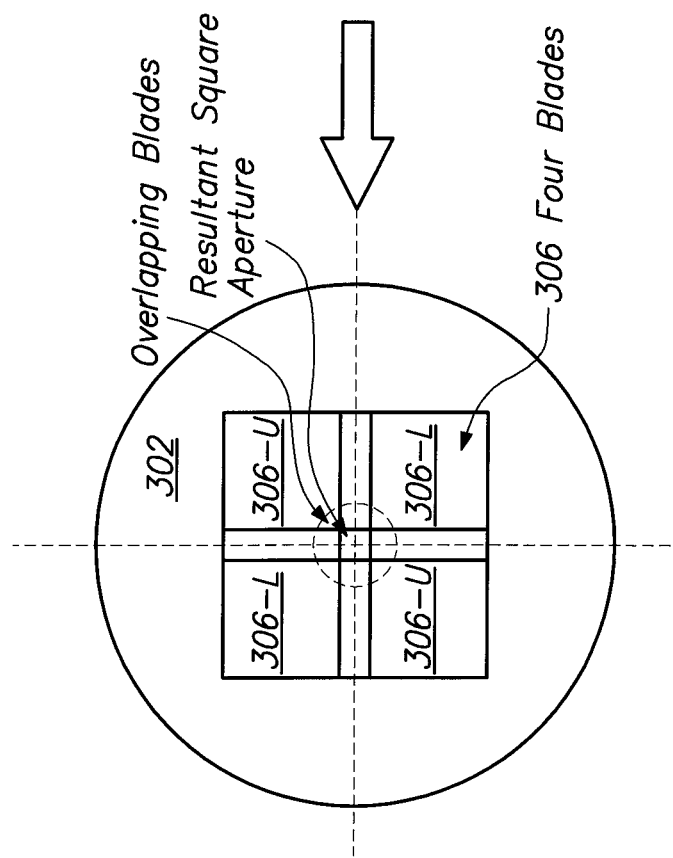

In the lower vacuum chamber, the primary electron beam 110 may pass through beam-current selection aperture which may be used to select a final beam current to the target substrate for imaging. In accordance with one embodiment of the invention, the beam-current selection aperture may comprise a continuously-variable aperture (CVA) 114. Example embodiments of the CVA 114 are described below in relation to FIGS. 3A, 3B and 3C. While a square-shaped CVA is depicted in FIGS. 3A, 3B and 3C, the CVA may be more generally implemented as an N-side aperture with N equal sizes, where N=3, 4, 5, 6, and so on. Innovative CVA designs are also described in commonly-owned U.S. patent application Ser. No. 13/006,999, filed Jan. 14, 2011, entitled "High-Vacuum Variable Aperture Mechanism and Method of Using Same."

The CVA 114 may be configured or adjusted to an optimized aperture size, $D_{opt}$. In accordance with an embodiment of the invention, the optimized aperture size may be indexed to a particular column condition domain. Two example column condition domains and their corresponding optimized aperture sizes are described below in relation to FIG. 4.

The primary electron beam 110 may be focused into a beam spot on the surface of the target substrate 118 by an objective lens (OL) 116. The objective lens 116 is preferably configured to have a very low spherical aberration coefficient and a very low chromatic aberration coefficient. The objective lens 116 may also retard the energy of (i.e. decelerate) the electrons in the primary beam from the "beam energy" (BE) level to a lower "landing energy" (LE) level. The particular energy levels to be used depend on the particular implementation.

The objective lens 116 may include, in a magnetic section, an inner pole piece and an outer pole piece, where the inner pole piece is depicted in FIG. 1. In accordance with an embodiment of the invention, the pole pieces of the objective lens 116 may be configured such that the target substrate 118 is heavily immersed in the magnetic field produced by the objective lens 116.

As shown, the objective lens 116 may also include, in an electrostatic section, an electrically-grounded (GND) plate 120 and a charge-control (CC) plate 122. The CC plate 122 may be used to establish the electric field (E-field) strength on the surface of the target substrate 118. The voltage applied to the CC plate 122 may be a positive or a negative voltage with respect to the ground plate 120.

In accordance with an embodiment of the invention, the electrostatic section of the objective lens 116 may also include a pre-charge-control (Pre-CC) 121 plate. The Pre-CC plate 121 may be positioned between the ground plate 120 and the CC plate 122. The voltage applied to the Pre-CC plate 121 may be varied to provide an additional degree of freedom so as to further minimize lens aberrations and further optimize charge control at the target substrate 118. In addition, the voltage applied to the Pre-CC plate 121 may be used to optimize the retardation (lowering) of the energy of the primary electron beam as it approaches the target substrate.

The primary electron beam 110 may be scanned over an area on the target substrate using a scanning system. The scanning system may comprise a dual-deflection scanner including a pre-scanner/stigmator 124 and a Wien filter/main scanner 126. The scanning system may be utilized to deflect the e-beam in the x and y directions (for example, in a raster pattern) so as to scan the beam over a region within the field of view of the imaging apparatus.

In one embodiment, the pre-scanner 124 and the main scanner 126 are both configured with a tapered shape. The shape of the scanners is tapered the thickness of the electrodes varies from a thicker end to a thinner end. The thicker end is configured closer to the manufactured substrate while the thinner end is configured closer to the electron source.

The impingement of the primary electron beam 110 into the surface of the target substrate 118 causes emission of secondary electrons 128. The secondary electrons are extracted from the target substrate 118 and deflected away from the z-axis by the Wien filter/main scanner 126. For example, the electrostatic deflection field for the Wien filter may be that generated by and used for the main scanning deflector, and the magnetic deflection field for the Wien filter may be generated by a two-pair saddle yoke with coils. The electrostatic and magnetic fields in the Wien filter are perpendicular and balanced such that the primary electron beam is not deflected while the secondary electrons are deflected.

A detector 130 may then detect the secondary electrons. The detector 130 may be positioned, for example, in between the pre-scanner 124 and the CVA 114. The secondary electron detection signal may be synchronized or coordinated with the primary electron scanning signal such that an image of the scanned area may be produced.

FIG. 3A shows a cross-sectional view of a square aperture with overlapping blades 306 in accordance with an embodiment of the invention. Applicants have determined that such a square aperture may be configured to form a continuously-variable aperture, and that such a continuously-variable aperture may contribute a further 10% to 100% improvement of resolution across column conditions ranging from landing energies of 50 to 5,000 eV and wafer electric fields ranging from −100 V/mm to +2,000 V/mm.

As seen, the aperture base 302 may comprise a circular hole 304 in a thinner section at its middle. The circular hole 304 may be oversized in that it is larger than the largest needed square aperture to be formed by the overlapping blades. In one implementation, the aperture base 302 may comprise a molybdenum round aperture.

The overlapping blades 306 may be supported by the top surface of the aperture base 302. The overlapping blades 306 may include at least one upper aperture blade 306-U and at least one lower aperture blade 306-L. In one implementation, the blades 306 may comprise thin molybdenum blades.

In some implementations, a spacer 307 may be configured between the base 302 and the upper aperture blade 306-U to raise the height of the upper aperture blade 306-U above that of the lower aperture blade 306-L. The thickness of the spacer 307 may be slightly thicker than the thickness of the lower aperture blade 306-L such that portions of the upper aperture blade 306-U may slide over the lower aperture blade 306-L without contact between the blades being made.

In accordance with an embodiment of the invention, a resultant square aperture 312 may be formed from a plan view perspective. The perimeter of the square aperture 312 may be formed from edges of the aperture blades 306 and may be centered on the electron-optical axis of the column.

FIG. 3B shows a plan view of a square aperture which is formed by overlapping two V-cut blades in accordance with an embodiment of the invention. The right side of the figure shows the individual aperture parts, and the left side of the figure shows the parts as they are put together to form the square aperture. As shown, the two blades 306 may be attached to the base 302 and/or spacer 307 by spot welding.

In this embodiment, the upper and lower blades (306-U and 306-L) each have a V-cut opening. When the blades are configured to form the square aperture, the edges of their V-cut openings form the perimeter of the square aperture. The upper and lower blades (306-U and 306-L) may be slid horizontally to increase or decrease their overlap. Increasing the overlap of the blades results in a smaller square aperture, while decreasing their overlap results in a larger square aperture.

FIG. 3C shows a plan view of a square aperture which is formed by overlapping four rectangular blades in accordance with an embodiment of the invention. The right side of the figure shows the individual aperture parts, and the left side of the figure shows the parts as they are put together to form the square aperture. As shown, the four blades 306 may be attached to the base 302 by spot welding.

In this embodiment, two of the blades are configured as lower blades 306-L and may be attached directly to the base 302, while the other two blades are configured as upper blades 306-U and may be attached on top of portions of the lower blades 306-L. For example, as indicated in plan view of FIG. 3C, the lower blades 306-L may be arranged above and below the center of the circular opening 304, while the upper blades 306-U may be arranged on the left and right of the center of the circular opening 304. As such, the edges of the four blades 306 form the perimeter of the square aperture. Increasing the overlap of the blades 306 results in a smaller square aperture, while decreasing their overlap results in a larger square aperture.

In accordance with one embodiment, the horizontal positioning of the blades 306 (configured as shown in either FIG. 3B or FIG. 3C, for example) may be driven electrically and measured by capacitative sensors mounted symmetrically around the center of the aperture. The aperture size may be changed from one size to another within a couple of seconds. Advantageously, such a square aperture is continuously variable in that its size may be continuously (rather than discretely) varied over a size range.

Figure 4:
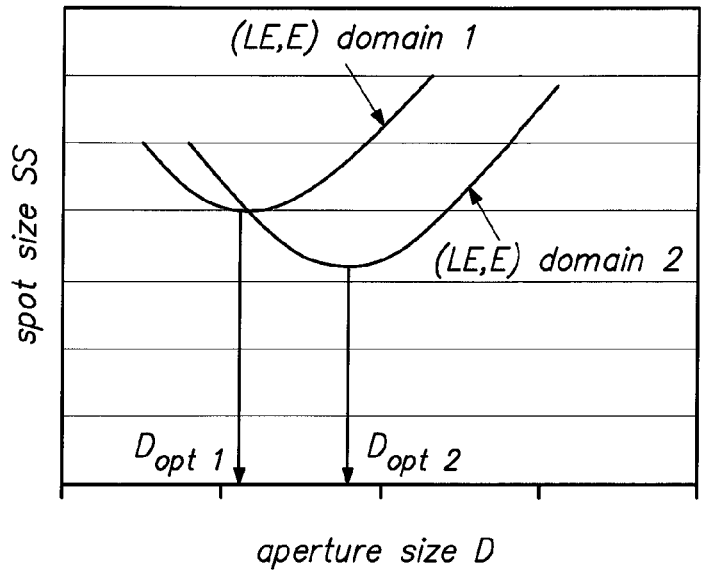
FIG. 4 is a graph showing spot size versus aperture size for two different column conditions (two different domains) in accordance with an embodiment of the invention.

FIG. 4 is a graph showing spot size versus aperture size for two different column conditions (two different domains) in accordance with an embodiment of the invention. The performance of an electron-beam inspection instrument may be characterized by spot size (SS) and beam current (BC), where the former represents the resolution of the instrument and the latter represents the throughput of the machine. The BC finally reaching the sample may be selected by a beam current selection aperture with aperture size D positioned in between the gun and objective lenses.

Inspections for different wafer layers normally require different column conditions, i.e. different electron landing energies (LE) on the wafer surface and different electric field strengths (E) applied on the wafer surface. Different column conditions, particularly in terms of different LE and E, are referred to herein as different domains. From an electron-optics point of view, the minimal SS for different column-condition (LE, E) domains requires different optimal apertures $D_{opt}$, even at the same BC. The optimal aperture size $D_{opt}$ fundamentally reflects a balance of optical blurs between lens aberrations and electron-electron interactions, where the electron-electron interactions are dominant when $D<D_{opt}$ while the lens aberrations are dominant when $D>D_{opt}$.

Given a particular BC, the optimal aperture size $D_{opt}$ may be determined to be the aperture size D where the SS is at a minimum. As shown in FIG. 4, the minimal SS may be found at the optimum aperture size $D_{opt1}$ for the curve for (LE, E) domain 1 and at the optimum aperture size $D_{opt2}$ for the curve for (LE, E) domain 2. In this example, the minimum SS for domain 2 is smaller than the minimum SS for domain 1.

A prior method utilizes one aperture size D (corresponding to a single BC) to cover the entire column-condition space in terms of (LE, E). However, given the discussion above, this prior method fails to minimize the spot size (SS) at every column condition across the entire (LE, E) space (because the optimal aperture sizes $D_{opt}$ are different at different (LE, E) domains even at the same BC). In accordance with one aspect of the present invention, the optimized aperture $D_{opt}$ is indexed to the (LE,E) domain in the spot size minimization.

In a preferred embodiment for wide applications, the LE and E are extended to a large column-condition range, e.g.: LE=50 eV to 5,000 eV and E=−100 V/mm to +2,000 V/mm respectively. The optimized apertures across the (LE, E) domain may be implemented with a variable aperture device or an aperture rod on which multi-apertures are installed for best fitting to different wafer layers of applications. Applicants believe that the presently-disclosed aperture domain concept (in which the optimized aperture size is indexed not only to the BC, but also to LE and E) and its use provide for improved resolution in terms of SS in a range of about 10% to 100% across the electron-beam inspection application condition space.

In one implementation, optimal aperture sizes may be determined given a selected beam current and a particular column-condition domain (which may be specified, for example, by the beam current, landing energy, and electric field strength on the surface of the target substrate). The data providing the optimal aperture size given a selected beam current and a particular column-condition may be stored in memory or other data storage which is accessible to the control system for the electron beam column. Subsequently, when a beam current is selected, the controller may cause the aperture size to be adjusted to the optimal aperture size which is associated with a particular column-condition domain being used. Furthermore, it is also contemplated that the column-condition domain may be adjusted (and the aperture size adjusted to the optimal aperture size for the resultant domain) so as to further decrease the beam spot size.

Figure 5:
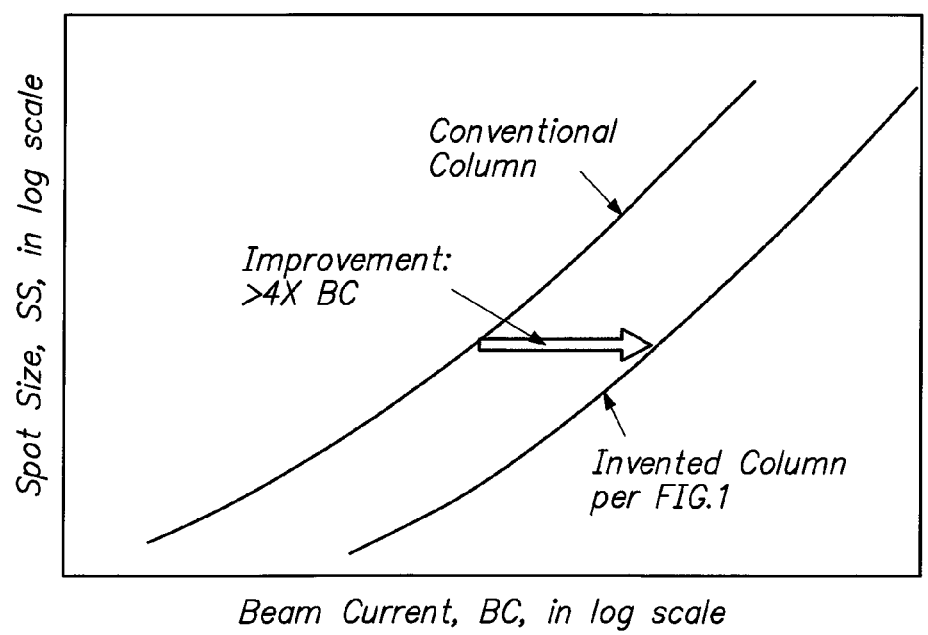
FIG. 5 is a graph showing an example of electron-optical performance improvement in accordance with an embodiment of the invention.

FIG. 5 is a graph showing an example of electron-optical performance improvement in accordance with an embodiment of the invention. Shown in FIG. 5 are plots of spot size (SS) versus beam current (BC), both in log scale, for a conventional column and for a column configured as disclosed herein per FIG. 1. As seen, at a same spot size, the column as disclosed herein per FIG. 1 has a higher beam current by more than four times over the conventional column.

FIGS. 6A-6D show computer simulations (computer modeling) of electron beam spots generated using a conventional circular aperture and using a square aperture in accordance with an embodiment of the invention. Lens aberrations and electron-electron interactions are included in the modeling.

Figure 6B:
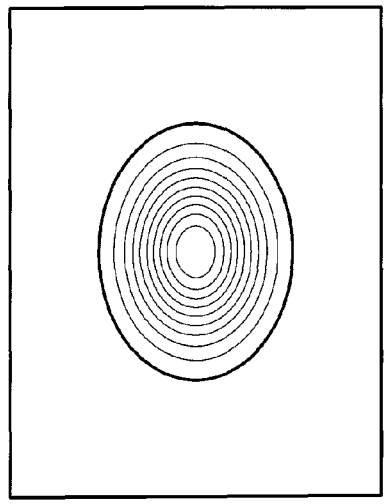
FIG. 6B shows two-dimensional contour modeling of a round aperture.
Figure 6D:
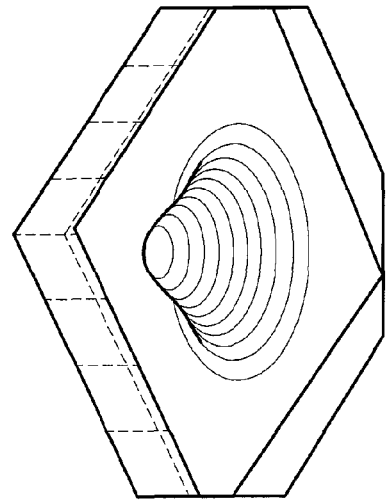
FIG. 6D shows three-dimensional profile modeling of a round aperture.
Figure 6A:
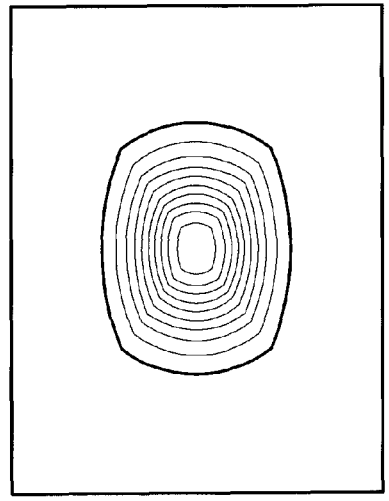
FIG. 6A shows two-dimensional contour modeling of a square aperture in accordance with an embodiment of the invention.
Figure 6C:
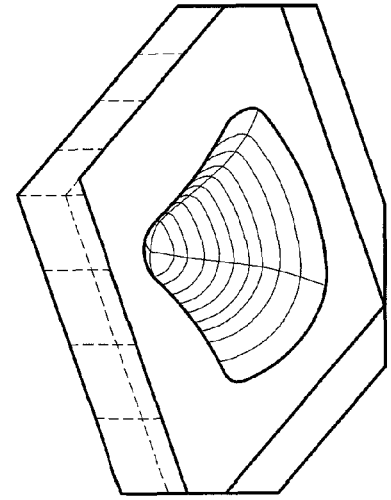
FIG. 6C shows three-dimensional profile modeling of a square aperture in accordance with an embodiment of the invention.

FIG. 6A shows two-dimensional contour modeling of a square aperture in accordance with an embodiment of the invention, while FIG. 6B shows two-dimensional contour modeling of a round aperture. FIG. 6C shows three-dimensional profile modeling of a square aperture in accordance with an embodiment of the invention, while FIG. 6D shows three-dimensional profile modeling of a round aperture. As seen from FIGS. 6A-6D, the electron beam spot generated using a square aperture is comparable to those generated using a circular aperture.

Figure 7:
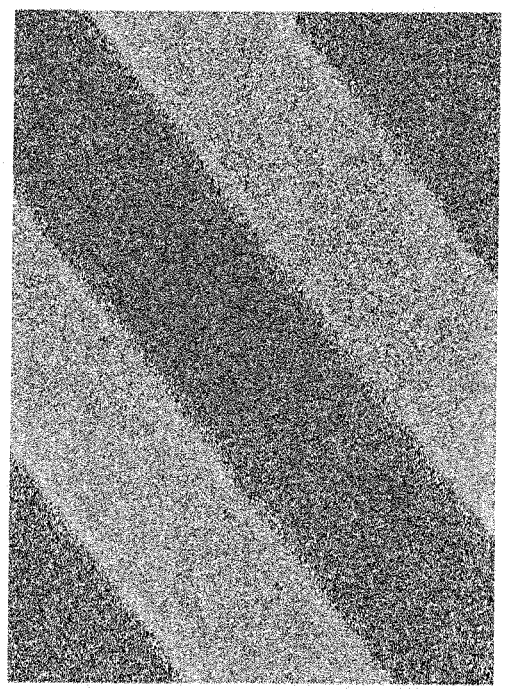
FIG. 7A shows an electron beam image obtained with a square aperture formed using overlapping blades in accordance with an embodiment of the invention.
FIG. 7B shows an electron beam image obtained with a round aperture.
Figure 7:
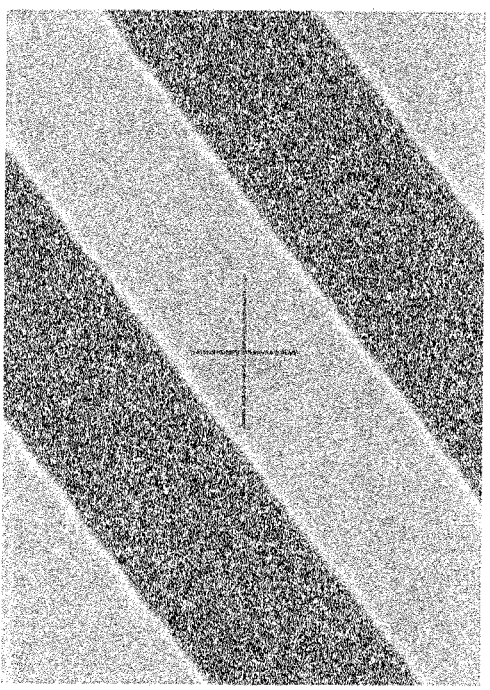

FIGS. 7A and 7B show electron images formed using a conventional circular aperture and using an overlapping square aperture in accordance with an embodiment of the invention. FIG. 7A shows an electron beam image obtained with a square aperture formed using overlapping blades in accordance with an embodiment of the invention. FIG. 7B shows an electron beam image obtained with a round aperture. As seen, there is no visible degradation in the image formed by the overlapping square aperture. In fact, the image formed by the overlapping square aperture appears to have less blurring and better resolution. Applicants have determined that there is no visible image degradation in the image formed by the overlapping square aperture even when using high beam currents.

CONCLUSION

Advantageously, by using the apparatus and methods disclosed herein, the electron-optics imaging resolution may be substantially improved, and/or the throughput for an electron inspection apparatus may be substantially increased.

The above-described diagrams are not necessarily to scale and are intended be illustrative and not limiting to a particular implementation. In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An electron beam column for automated inspection of manufactured substrates, the electron beam column comprising:
   an electron gun including a source for emitting electrons and a gun lens for focusing the electrons into an electron beam;
   an objective lens for focusing the electron beam onto a beam spot on a surface of a target substrate;
   a continuously-variable aperture configured to select a beam current;
   a ground plate below the objective lens;
   a charge-control plate above the surface of the target substrate; and
   a pre-charge control plate between the ground plate and the charge-control plate.

2. The electron beam column of claim 1, wherein the continuously-variable aperture is formed by overlapping blades.

3. The electron beam column of claim 2, wherein the overlapping blades form a square aperture.

4. The electron beam column of claim 3, wherein V-cut edges of two blades form the square aperture.

5. The electron beam column of claim 3, wherein edges of four blades form the square aperture.

6. The electron beam column of claim 1, further comprising:
   a gate valve configured between the electron gun and the continuously-variable aperture.

7. A method of using an electron beam column for automated inspection of manufactured substrates, the method comprising:
   emitting electrons from a source;
   forming an electron beam using a gun lens to focus the electrons;
   selecting a beam current using a continuously-variable aperture;
   focusing the electron beam onto a beam spot on a surface of a target substrate using an objective lens;
   applying a voltage to a pre-charge control plate between a ground plate below the objective lens and a charge control plate above the target substrate;
   scanning the beam spot over the surface of the target substrate; and
   detecting secondary electrons from the beam spot using a detector.

8. The method of claim 7, further comprising:
   adjusting an aperture size of the continuously-variable aperture by changing an amount of overlap between overlapping blades.

9. The method of claim 8, wherein the overlapping blades form a square aperture.

* * * * *